US006991658B2

(12) United States Patent
Slemker et al.

(10) Patent No.: US 6,991,658 B2
(45) Date of Patent: Jan. 31, 2006

(54) FLEXION CONTRACTURE TKA ADAPTOR (75) Inventors: Tracy C. Slemker, Clayton, OH (US); Scott R. Schall, Englewood, OH (US)

(73) Assignee: Prosthetic Design, Inc., Clayton, OH (US)

( * ) Notice: Subject to any disclaimer, the term of this patent is extended or adjusted under 35 U.S.C. 154(b) by 0 days.

(21) Appl. No.: 10/243,200

(22) Filed: Sep. 13, 2002

(65) Prior Publication Data
US 2003/0074085 A1    Apr. 17, 2003

Related U.S. Application Data

(60) Provisional application No. 60/328,559, filed on Oct. 11, 2001.

(51) Int. Cl.
*A61F 2/80* (2006.01)
(52) U.S. Cl. ...................................................... 623/38
(58) Field of Classification Search ................. 623/38, 623/27, 28, 47, 49; 248/300; 606/69
See application file for complete search history.

(56) References Cited

U.S. PATENT DOCUMENTS

| | | | | |
|---|---|---|---|---|
| 4,299,020 A | * | 11/1981 | Grego, Jr. | 29/259 |
| 4,800,874 A | * | 1/1989 | David et al. | 128/92 Y |
| 4,822,363 A | * | 4/1989 | Phillips | 623/27 |
| 5,904,684 A | * | 5/1999 | Rooks | 606/69 |
| 5,997,583 A | * | 12/1999 | Woolnough et al. | 623/38 |
| 6,508,819 B1 | * | 1/2003 | Orbay | 606/69 |
| 2002/0193887 A1 | * | 12/2002 | Swanson | 623/36 |

FOREIGN PATENT DOCUMENTS

| | | |
|---|---|---|
| CH | 638 095 | 9/1983 |
| FR | 77 37947 | 7/1979 |
| GB | 1 208 421 | 10/1970 |
| WO | WO 95/30391 | * 11/1995 |

OTHER PUBLICATIONS

John Michael, "Long Transfemoral Amputation + Flexion Contracture + Shuttle Lock = Fabrication Nightmare", website article, Jul. 2002, Oandp.com, O&P Digital Technologies, Gainesville, Florida, USA.

"PEL Supply Distributes RapidFit", AO&P Almanac, Sep., 2002, The American Orthotic & Prosthetic Association, Alexandria, Virginia, USA.

Catalog page depicting 1/2" and 3/4" offset plate components, date: N/A (however, applicant admits that the displayed offset plate components are prior art with respect to the present invention); Prosthetic Design, Inc., Clayton, Ohio, USA.

* cited by examiner

*Primary Examiner*—Bruce Snow
(74) *Attorney, Agent, or Firm*—Taft Stettinius & Hollister, LLP (57) ABSTRACT

An interconnection component or an adaptor bracket for use in coupling a distal end of a prosthetic limb socket to a proximal end of an endoskeletal component of a prosthetic limb, where the interconnection component is specifically adapted to compensate for a patient's flexion contracture.

14 Claims, 5 Drawing Sheets

| X Offset (inches) | | TD Limb Length, Trocanter to Distal (inches) | | | | | | | | | |
|---|---|---|---|---|---|---|---|---|---|---|---|
| | | 5 | 6 | 7 | 8 | 9 | 10 | 11 | 12 | 13 | 14 |
| Degree Of Flexion Contracture From Vertical θ | 5 | 0.436 | 0.523 | 0.61 | 0.697 | 0.784 | 0.872 | 0.959 | 1.046 | 1.133 | 1.22 |
| | 10 | 0.868 | 1.042 | 1.216 | 1.389 | 1.563 | 1.736 | 1.91 | 2.08 | 2.257 | 2.431 |
| | 15 | 1.294 | 1.553 | 1.812 | 2.07 | 2.329 | 2.59 | 2.847 | 3.11 | 3.365 | 3.623 |
| | 20 | 1.71 | 2.052 | 2.394 | 2.736 | 3.078 | 3.42 | 3.762 | 4.104 | 4.446 | 4.788 |

TABLE 1

FIG. 6

FLEXION CONTRACTURE TKA ADAPTOR

CROSS REFERENCE TO RELATED APPLICATIONS

This application claims the benefit of U.S. Provisional Patent Application No. 60/328,559, filed Oct. 11, 2001, the disclosure of which is incorporated herein by reference.

BACKGROUND

The present invention relates generally to prosthetic devices, and more particularly, to a coupling component for use in coupling a prosthetic limb socket assembly to a prosthetic limb upright assembly, that is specifically adapted to compensate for flexion contracture of a patient's residual limb.

Figure 1:
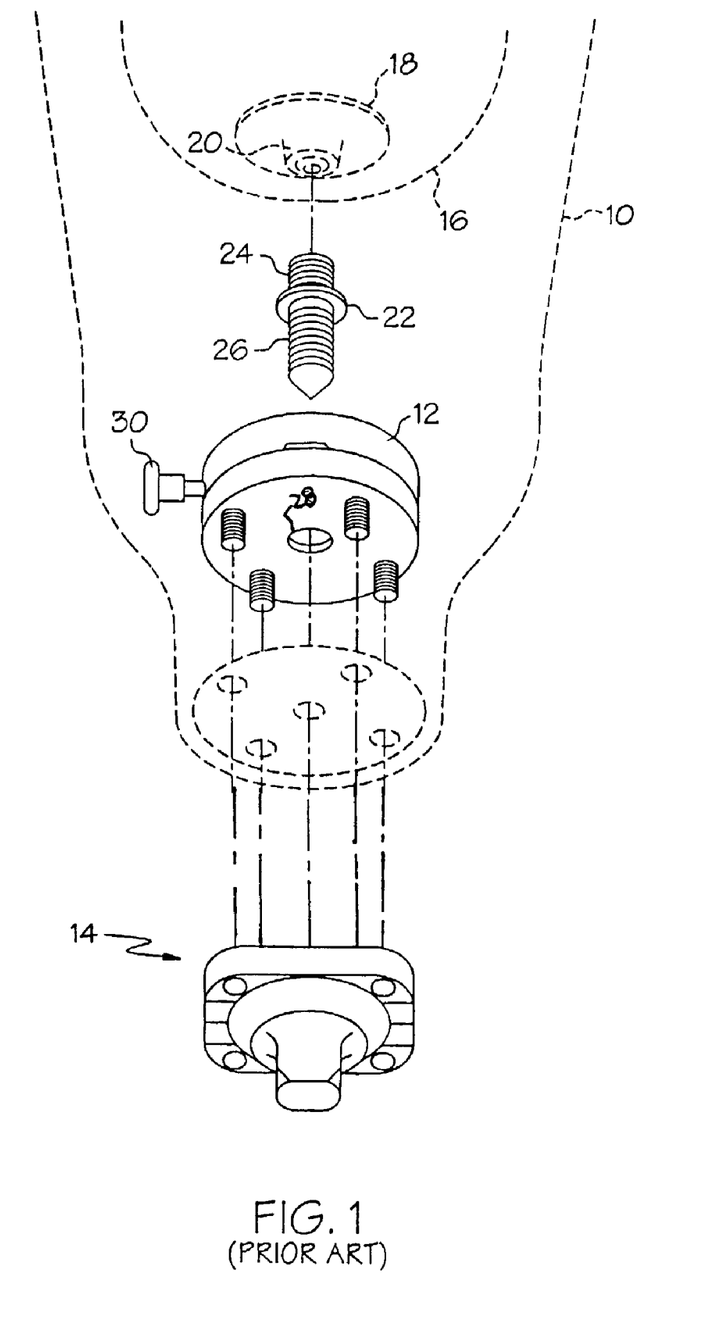
FIG. 1 is an exploded perspective view of an example prior art socket assembly for a prosthetic limb.

FIG. 1 shows an example of a prior art socket assembly for a prosthetic limb. The prior art socket assembly includes a rigid molded plastic socket 10 sized and shaped to receive a patient's residual limb therein, a locking device 12 (such as a "shuttle lock") positioned at the distal end of the rigid socket 10, interconnection components 14 for maintaining the lock 12 within the socket 10 and for mounting other components of the prosthetic limb to the distal end of the socket, and a silicone sleeve 16 adapted to be snugly fitted (rolled onto) the patient's residual limb. The silicone sleeve 16 includes a plate 18 molded therein having an internally threaded boss 20 extending therefrom. A plunger pin 22 includes an externally threaded proximal end 24 adapted to be attached to the internally threaded boss 20 of the attachment plate 18 and includes a ratcheted distal end 26 that is adapted to be received within the center hole 28 of the lock 12 and to be locked within the center hole by a spring-loaded pawl (not shown).

Figure 2:
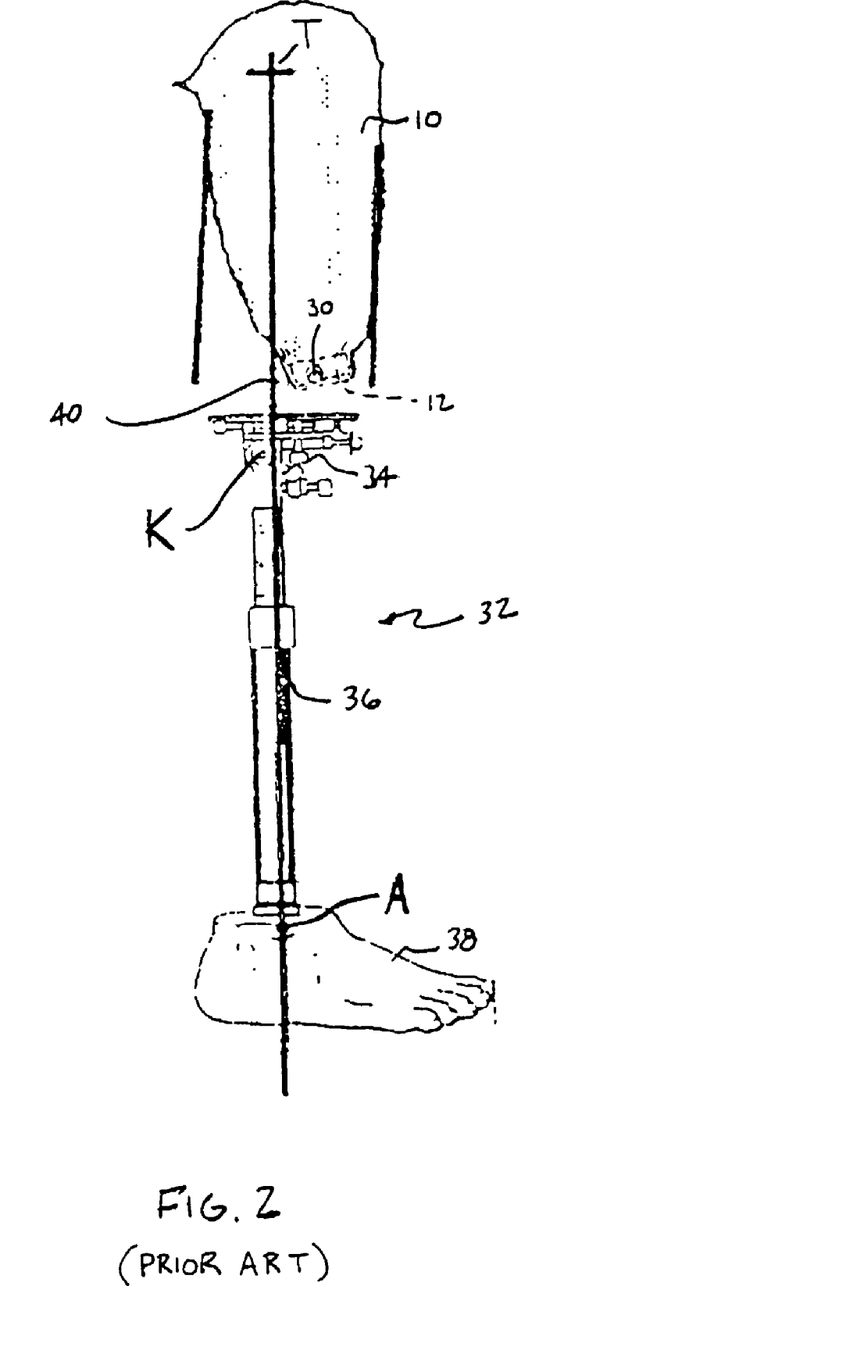
FIG. 2 is an elevational side view of an example prior art prosthetic limb assembly, where the patient's residual limb experiences substantial flexion contracture.
Figure 3A:
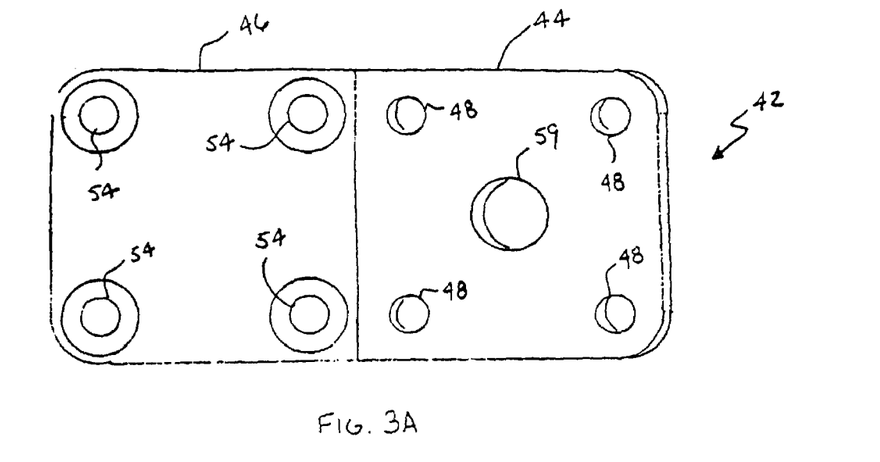
FIG. 3A is a top plan view of a coupling adaptor according to an exemplary embodiment of the present invention.
Figure 3B:
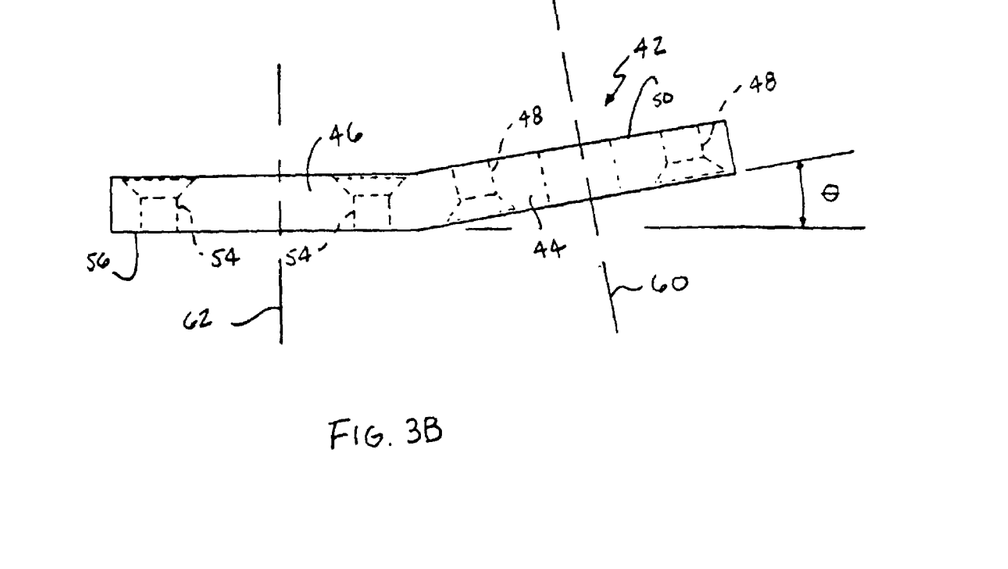
FIG. 3B is a side elevational view of the coupling adaptor of FIG. 3A.
Figure 4A:
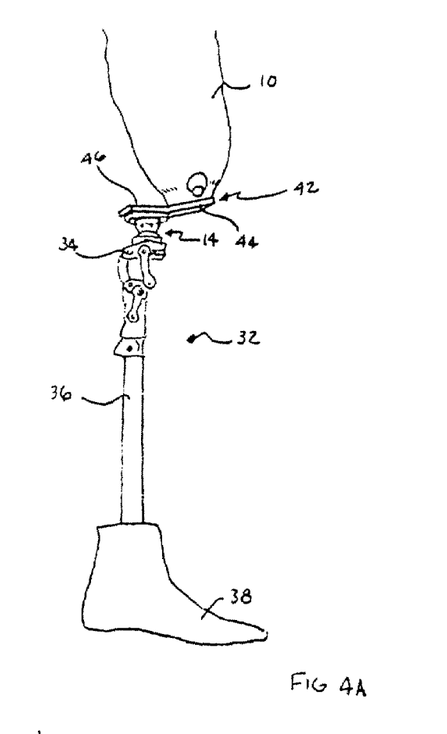
FIG. 4A is a perspective view of a prosthetic limb assembly utilizing the exemplary embodiment of the coupling adaptor.
Figure 4B:
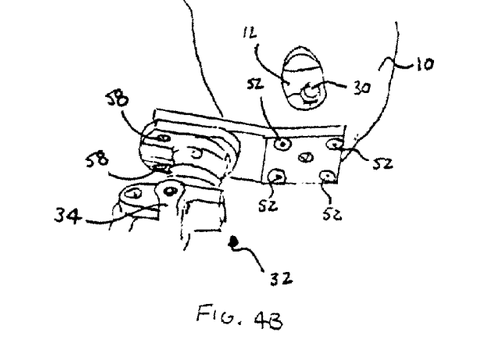
FIG. 4B is a perspective view of a prosthetic limb assembly utilizing the exemplary embodiment of the coupling adaptor, where the view is magnified on the coupling adaptor.

To don the prosthetic limb, the patient will roll on or slip on the silicone sleeve 16 so that the plunger pin 22 extends distally from the patient's residual limb and will then insert the residual limb into the plastic socket 10 such that the plunger pin 22 engages with the lock 12. To release the plunger pin 22 from the lock 12, a button 30 on the lock is activated to remove the pawl from within the center hole 28, thereby releasing the ratcheted distal end 26 of the plunger pin from within the center hole 28. Referring to FIG. 2, the interconnection components (not shown in FIG. 2) will be utilized to couple the distal end of the socket 10 to the proximal end of the upright assembly 32 of the prosthetic limb. For the purposes of the present application, the upright assembly is all components, or combination of components, coupled to the distal end of the prosthetic limb socket. The upright assembly, in this example, includes a prosthetic knee joint 34, coupled to the proximal end of a leg shaft 36, which is, in turn, coupled to a proximal end of a prosthetic foot component 38. Another example of an upright assembly may merely comprise a prosthetic foot assembly.

Acceptable alignment for a transfemoral patient's prosthesis is to align, from the lateral side, the Trocanter (T), Knee axis (K) and Ankle axis (A) in a vertical line, illustrated by numeral 40. There are many different types and designs of modular attachment components for use in coupling the distal surface of the prosthetic limb socket 10 to the proximal end of the knee chassis 34. Some of these components offer angular, rotational and horizontal translational adjustments independently that allow the prosthetist to align the prosthesis and maintain a proper alignment or TKA line. If the TKA line is not maintained, normal gait may be unachievable. TKA alignment for a prosthetic limb is even more troublesome in cases where the patient's residual limb experiences a substantial amount of flexion contracture, which can be defined as the angle between the body weight line perpendicular to the ground and the bisector line of the lateral aspect of the flexed residual limb.

If a prosthetist were to use a sliding/rotating pyramid receiver (commercially available from Prosthetic Design, Inc., p/n PR-SL-R, described in U.S. patent application Ser. No. 09/613,977, entitled COUPLING-SOCKET ADAPTOR ASSEMBLY FOR A PROSTHETIC LIMB) and a fixed pyramid connector for coupling the proximal end of the knee chassis 34 to the distal end of the prosthetic limb socket 10, the prosthetist would be able to slide the sliding/rotating pyramid receiver up to one-half inch (½") off-center in either a medial/lateral direction or an anterior/posterior direction. In addition, the prosthetist would have angular adjustments available up to ten degrees (10°) and unlimited rotational adjustments. However, if a transfemoral amputee has a flexion contracture of ten degrees (10°) and a residual limb length of twelve inches (12") trocanter to the distal surface of the socket, the attachment components need to accommodate the ten degree angle and an offset of 2.08 inches (2.08"). Since there are no commercially available attachment components that feature a drastic offset an angle to maintain the TKA line, the prosthetist and/or technician would need to fabricate the prosthesis in a way that incorporates the offset angle for the patient that has flexion contracture. A problem with this custom fabrication, is that the process for fabricating the prosthesis to incorporate an offset of 2.08 inches and ten degrees flexion contracture, for example, is very labor-intensive, time consuming and challenging.

SUMMARY

The present invention provides an interconnection component or an adaptor bracket for use in coupling a distal end of a prosthetic limb socket to a proximal end of an upright assembly component (an endoskeletal component) of a prosthetic limb, where the interconnection component is specifically adapted to compensate for a patient's flexion contracture. The interconnection component includes a generally planar proximal surface with a first coupling and a generally planar distal surface with a second coupling, where the generally planar proximal surface is angled with respect to the generally planar distal surface at an angle compensating for the patient's flexion contracture, and where the first coupling is laterally spaced from (or set-apart from) the second coupling at a lateral distance compensating for the patient's flexion contracture.

It is a first aspect of the present invention to provide a bracket for use in coupling a prosthetic limb socket component to a prosthetic limb endoskeletal component that includes: (a) a first generally planar segment, including a first coupling adapted for mounting to a distal end of a prosthetic limb socket; and (b) a second generally planar segment, offset from the first generally planar segment and angled with respect to the first generally planar segment at a pre-determined angle, including a second coupling adapted for mounting to a proximal end of a endoskeletal component. In a more specific embodiment, the pre-determined angle between the first and second generally planar segments is determined, at least in part, upon an angle of a patient's flexion contracture. In a further detailed embodiment, the offset between the first and second generally planar segments is determined, at least in part, upon the angle of the patient's flexion contracture and the length of the patient's residual limb. In a further detailed embodiment, the offset "X" between the first and second generally planar segments is determined, at least in part, upon the following equation:

$$X = (TD)\sin\theta$$

where TD is the distance between the patient's trocanter and a distal end of the prosthetic limb socket when donned by the patient, and where "θ" is the angle of the patient's flexion contracture. In a further detailed embodiment, the first and second planar segments comprise a single plate folded into segments at a pre-determined angle. In yet a further detailed embodiment, the first coupling includes a plurality of through holes uniformly distributed about a first coupling axis and the second coupling includes a plurality of through holes uniformly distributed about a second coupling axis. In a further detailed embodiment, the angle between the first and second coupling axes is substantially equal to an angle of a patient's flexion contracture. In a further detailed embodiment, the plate is formed from a rigid metallic material such as aluminum or a resilient material such as carbon graphite. The resilient, or flexible carbon graphite material allows the knee to flex slightly under weight bearing forces, it absorbs shock, it conserves energy, and it therefore normalizes gait.

In an alternate detailed embodiment of the first aspect of the present invention, the first and second planar segments comprise a single plate folded into two segments at a pre-determined angle. In a further detailed embodiment, the first coupling includes a plurality of through holes uniformly distributed about a first coupling axis and the second coupling includes a plurality of through holes uniformly distributed about a second coupling axis. In yet a further detailed embodiment, the angle between the first and second coupling axes is substantially equal to an angle of a patient's flexion contracture.

It is a second aspect of the present invention to provide a coupling adaptor for use in coupling a distal end of a proximal prosthetic limb component to a proximal end of a distal prosthetic limb component that includes: (a) a body having a proximal end and a distal end, where the body includes a first coupling adapted to mount the body to a distal end of the proximal prosthetic limb component so that the distal end of the proximal prosthetic limb component extends from the body along a first axis, and the second coupling adapted to mount the body to a proximal end of the distal prosthetic limb component so that the distal prosthetic limb component extends from the body along a second axis; where an intersection point between the first coupling and the first axis is laterally spaced from the intersection point between the second coupling and the second axis; and where the first axis is angled with respect to the second axis. In a detailed embodiment, the angle between the first axis and the second axis is determined based, at least in part, upon an angle of a patient's flexion contracture. In a further detailed embodiment, the angle between the first axis and the second axis is approximately the same as the angle of the patient's flexion contracture. In a further detailed embodiment, the lateral spacing between the intersection point between the first coupling and the first axis and the intersection point between the second coupling and the second axis is determined based, at least in part, upon a length of a patient's residual limb and upon an angle of a patient's flexion contracture. In a further detailed embodiment, the angle between the first axis and the second axis is approximately the same as the angle between the patient's flexion contracture. In yet a further detailed embodiment, the first coupling includes a plurality of screw- or bolt-receiving holes extending into a proximal end the body and uniformly distributed about the first axis and the second coupling includes a plurality of screw- or bolt-receiving holes extending into a distal end of the body and uniformly distributed about the second axis. In yet a further detailed embodiment, the body is a planar member bent into two segments, the first of the segments including the first coupling and the second of the segments including the second coupling.

It is a third aspect of the present invention to provide an interconnection component for use in coupling a prosthetic limb socket assembly or component to a prosthetic limb endoskeletal assembly or component that includes: a multi-segment bracket including (a) a generally planar proximal surface including a first coupling adapted for mounting to a distal end of a prosthetic limb socket assembly or component; and (b) a generally planar distal surface including a second coupling adapted for mounting to a proximal end of a prosthetic limb endoskeletal assembly or component; where the generally planar distal surface is offset from the generally planar proximal surface and where the generally planar distal surface is angled with respect to the generally planar proximal surface so as to be adapted to improve TKA alignment problems of the patient's residual limb caused by residual limb flexion contracture.

It is a fourth aspect of the present invention to provide a method for coupling a prosthetic limb socket assembly to a prosthetic limb upright assembly and for substantially compensating flexion contracture of the patient's residual limb. The method includes the steps of: (a) providing a bracket including a first generally planar segment having a first coupling and a second generally planar segment having a second coupling, where the second generally planar segment is angled with respect to the first generally planar segment at an angle compensating for the patient's flexion contracture, and the first coupling is laterally spaced from the second coupling at a lateral distance compensating for the patient's flexion contracture; (b) coupling the distal end of the patient's residual limb socket to the first coupling; and (c) coupling the proximal end of the patient's prosthetic limb upright assembly to the second coupling.

DETAILED DESCRIPTION

As shown in FIGS. 3A, 3B, 4A and 4B, an exemplary embodiment of a coupling adaptor or bracket 42 according to an exemplary embodiment of the present invention is provided. The bracket 42 is adapted to couple a distal end of a patient's socket assembly to a proximal end of a patient's endoskeletal upright assembly and to compensate for flexion contracture of the patient's residual limb, maintaining a TKA line for most flexion contracture transfemoral amputees. The bracket 42 includes a first generally planar segment 44 adapted to be coupled to a distal end of a patient's residual limb socket and a second generally planar segment 46 adapted to be coupled to a proximal end of a patient's endoskeletal upright assembly 32. The first planar segment 44 includes a first coupling, in the form of four bolt- or screw-receiving through holes 48, specifically adapted for coupling a distal end of a prosthetic limb socket assembly 10 to the proximal surface 50 of the bracket 42 using screws or bolts 52. The second generally planar segment 46 includes a coupling, also in the form of four bolt- or screw-receiving through holes 54 and adapted to couple a distal surface 56 of the second planar segment 46 to a proximal end of a prosthetic limb upright assembly 32 using screws or bolts 58. The through-hole 59 in the first generally planar segment 44 is provided to allow a plunger-pin 26 extending through the socket assembly to be received.

The bracket 42 may be constructed of a rigid, metallic material such as aluminum or platinum; or, alternatively, the bracket 42 may be constructed partially or wholly from a more resilient and flexible material such as carbon graphite. The more resilient and flexible carbon graphite material would provide the bracket 42 with shock-absorption capabilities, and the carbon graphite material is also lighter than an aluminum or platinum material. Additionally, when the bracket is coupled to a proximal end of a knee component, the resilient, or flexible carbon graphite material allows the knee to flex slightly under weight bearing forces, it absorbs shock, it conserves energy, and it therefore normalizes gait.

Figure 5:
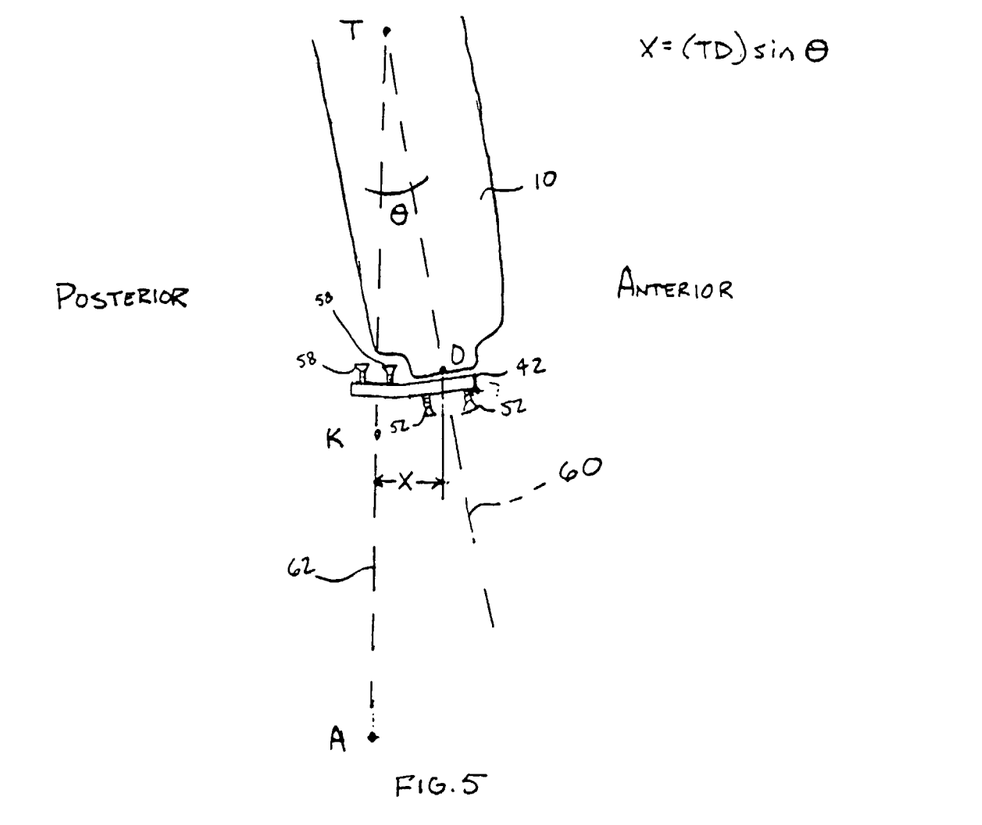
FIG. 5 is a schematic view of a coupling adaptor according to an exemplary embodiment of the present invention in use with a prosthetic limb socket.

As shown in FIG. 5, the first coupling is adapted to mount the bracket 42 to a distal end of the socket assembly 10 so that the distal end of the socket assembly 10 extends from the bracket 42 along a first axis 60 (in the present embodiment, the axis 60 extends through a center-point about which the through holes 48 are uniformly distributed). The second coupling mounts the bracket 42 to a proximal end of the prosthetic limb upright assembly 32 so that the prosthetic limb upright assembly 32 extends from the bracket 42 along a second axis 62 (the second axis 62, in the present embodiment, extends through the center-point about which the through holes 54 are uniformly distributed). This second axis 62 would typically be the TKA line. The first planar segment 44 is angled with respect to the second planar segment 46 and the center point of the first coupling (intersecting axis 60) and a center-point of the second coupling (intersecting axis 62) are laterally spaced from one another to compensate for the flexion contracture of the patient's residual limb.

Figure 6:
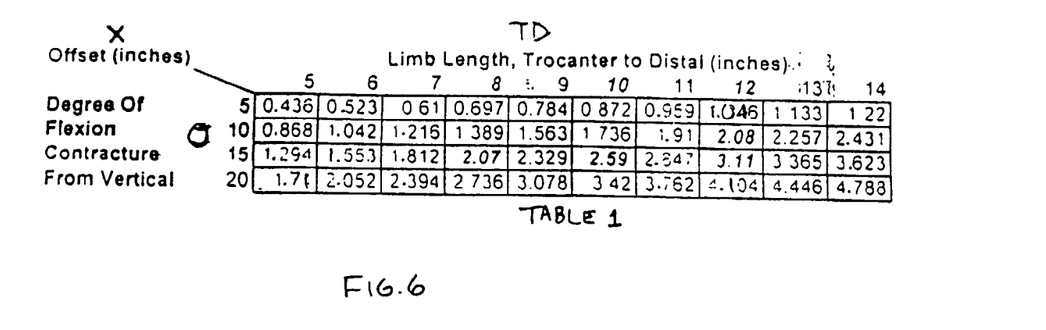
FIG. 6 provides a table for determining the offset for the coupling adaptor based upon the degree of flexion contracture and upon the limb length.

As shown in FIG. 6, Table 1 provides the lateral spacing or offset "X" between the center points of the first and second couplings, which is based upon the angle of flexion contracture "θ" and upon the length of the patient's residual limb "TD". More specifically, this lateral spacing "X" is based upon the distance "TD" between the patient's trocanter "T" and the distal end of the patient's residual limb socket "D" multiplied by sine of the angle of the patient's trocanter "θ", as shown in the equation below:

$$X = (TD) \sin \theta \qquad \text{Equ. 1}$$

Table 1 provides the lateral spacing X for several different degrees of flexion contracture (θ) versus several different limb length measurements (TD). For efficiency, the manufacturer may choose to sell only a few different versions of the bracket 42 that meet some of the more common contraction angles and limb lengths. Any additional variance may be compensated by the adjustable interconnection components, such as the sliding/rotating pyramid receiving component described above.

Following from the above detailed description, it will be apparent to those of ordinary skill in the art that, while the apparatuses and processes herein described constitute exemplary embodiments of the present invention, it is understood that the invention is not limited to these precise apparatuses and processes and that changes may be made therein without departing from the scope of the invention as claimed or as illustrated by the various aspects of the present invention set forth in the summary. Additionally, it is to be understood that the invention is defined by the claims and it is not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A coupling adaptor for use in coupling a distal end of a proximal prosthetic limb component to a proximal end of a distal prosthetic limb component, comprising:
    a body having a proximal end and a distal end, the body including a first coupling adapted to mount the body to a distal end of a proximal prosthetic limb component so that the distal end of the proximal prosthetic limb component extends lengthwise from the body along a first axis, and a second coupling adapted to mount the body to a proximal end of a distal prosthetic limb component so that the distal prosthetic limb component extends lengthwise from the body along a second axis;
    wherein an intersection point between the first coupling and the first axis is laterally spaced from the intersection point between the second coupling and the second axis; and
    wherein the first axis is angled with respect to the second axis ranging between one and about twenty-five degrees;
    wherein the first axis and the second axis intersect proximally with respect to the proximal end of the body;
    wherein the body maintains the relative orientation of the proximal prosthetic limb component with respect to the distal prosthetic limb component; and
    wherein an angle between the first axis and the second axis is determined based, at least in part, upon an angle of a patient's residual limb flexion contracture.

2. The coupling adaptor of claim 1, wherein the lateral spacing between the intersection point between the first coupling and the first axis and the intersection point between the second coupling and the second axis is determined based, at least in part, upon a length of a patient's residual limb and upon the angle of a patient's residual limb flexion contracture.

3. The coupling adaptor of claim 2, wherein the lateral spacing between the intersection point between the first coupling and the first axis and the intersection point between the second coupling and the second axis is approximately 0.436 inches to approximately 4.788 inches.

4. The coupling adaptor of claim 1, wherein the first coupling includes a plurality of screw- or bolt-receiving holes extending into a proximal end of the body and uniformly distributed about the first axis and wherein the second coupling includes a plurality of screw- or bolt-receiving holes extending into a distal end of the body and uniformly distributed about the second axis.

5. The coupling adaptor of claim 4, wherein the body is a planar member bent into two segments, a first of the segments including the first coupling and a second of the segments including the second coupling.

6. The coupling adaptor of claim 5, wherein the planar member is made substantially from a rigid metallic material.

7. The coupling adaptor of claim 5, wherein the planar member is made substantially from a resilient material.

8. The coupling adaptor of claim 7, wherein the planar member is made substantially from a carbon graphite material.

9. The coupling adaptor of claim 1, wherein:
the proximal prosthetic limb component is one of a prosthetic limb socket assembly and a prosthetic limb socket component; and
the distal prosthetic limb component is one of a prosthetic limb upright assembly, a prosthetic knee component, a prosthetic knee joint, and a prosthetic foot component.

10. A coupling adaptor for use in coupling a distal end of a prosthetic limb socket assembly to a proximal end of a prosthetic limb upright assembly, comprising:
an adaptor structure having a socket mating region adapted to be mounted to a distal end of the prosthetic limb socket assembly along a first axis generally perpendicular to the socket mating region and having an upright assembly mating region adapted to be mounted to a proximal end of the prosthetic limb upright assembly along a second axis generally perpendicular to the upright assembly mating region, where the prosthetic limb upright assembly includes a prosthetic knee joint;
wherein a first intersection point between the socket mating region and the first axis is horizontally spaced from a second intersection point between the upright assembly mating region and the second axis to compensate, at least in part, for a patient's flexion contracture;
wherein the first axis and the second axis intersect proximally with respect tote proximal end of the adapter structure;
wherein the adapter structure maintains the relative orientation of the prosthetic limb socket with respect to the proximal end of the prosthetic limb upright assembly;
wherein the first axis is angled with respect to the second axis to compensate, at least in part, for a patient's flexion contracture; and
wherein the first axis is angled with respect to the second axis at an angle of approximately 5° to approximately 20°.

11. The coupling adaptor of claim 10, wherein the first intersection point is horizontally spaced from the second intersection point at a distance from approximately 0.436 inches to approximately 4.788 inches.

12. The coupling adaptor of claim 10, wherein the adaptor structure is a unitary structure.

13. The coupling adaptor of claim 10, wherein the adaptor structure includes a resilient material adapted to provide shock absorption between the prosthetic limb socket assembly and the prosthetic limb upright assembly.

14. The coupling adaptor of claim 13, wherein the resilient material is a carbon graphite material.

* * * * *

UNITED STATES PATENT AND TRADEMARK OFFICE
CERTIFICATE OF CORRECTION

PATENT NO. : 6,991,658 B2  Page 1 of 1
APPLICATION NO. : 10/243200
DATED : January 31, 2006
INVENTOR(S) : Slemker et al.

It is certified that error appears in the above-identified patent and that said Letters Patent is hereby corrected as shown below:

Column 8, line 14, "tote" should be changed to --to the--.

Signed and Sealed this

Seventeenth Day of March, 2009

JOHN DOLL
*Acting Director of the United States Patent and Trademark Office*